(12) United States Patent
Davison et al.

(10) Patent No.: US 8,540,746 B2
(45) Date of Patent: *Sep. 24, 2013

(54) CANNULA FOR RECEIVING SURGICAL INSTRUMENTS

(75) Inventors: Thomas W. Davison, North Attleboro, MA (US); Timothy E. Taylor, Hoover, AL (US); Adam Sher, North Attleboro, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/615,961

(22) Filed: Sep. 14, 2012

(65) Prior Publication Data

US 2013/0066160 A1 Mar. 14, 2013

Related U.S. Application Data

(63) Continuation of application No. 11/417,616, filed on May 3, 2006, now Pat. No. 8,317,817, which is a continuation of application No. 10/440,278, filed on May 16, 2003, now Pat. No. 7,108,705, which is a continuation of application No. 09/772,605, filed on Jan. 30, 2001, now Pat. No. 6,800,084, which is a continuation-in-part of application No. 09/137,335, filed on Aug. 20, 1998, now Pat. No. 6,187,000.

(51) Int. Cl.
 *A61M 29/00* (2006.01)
(52) U.S. Cl.
 USPC ....................................................... 606/198
(58) Field of Classification Search
 USPC ............... 600/184, 201, 210, 211, 214, 215, 600/227, 234; 604/164.01, 164.11, 264; 606/86 A, 90, 105, 190, 279
 See application file for complete search history.

(56) References Cited

U.S. PATENT DOCUMENTS

| | | |
|---|---|---|
| 465,161 A | 12/1891 | Chase |
| 1,170,324 A | 2/1916 | Pomerene |
| 2,235,979 A | 3/1941 | Brown |

(Continued)

FOREIGN PATENT DOCUMENTS

| | | |
|---|---|---|
| AU | 1367295 A | 9/1995 |
| DE | 1566116 A1 | 1/1970 |

(Continued)

OTHER PUBLICATIONS

Synthes Spine, "Synthes Spine Top Loading System: Click X," Technique Guide, 2000.

(Continued)

*Primary Examiner* — Ryan Severson
*Assistant Examiner* — Jonathan W Miles
(74) *Attorney, Agent, or Firm* — Seager, Tufte & Wickhem, LLC

(57) ABSTRACT

A cannula (10) receives surgical instruments (120) for performing a surgical procedure on a body (130). The cannula (10) comprises a tube structure (12) defining a passage (16) through which the surgical instruments (120) are inserted into the body (130). The tube structure (12) has a proximal end (20) and a distal end (62). The tube structure (12) includes an expandable portion (40) for enabling an increase in the cross-sectional area of the passage (16) at the distal end (62). The expandable portion (40) of the tube structure (12), when expanded, has a conical configuration.

10 Claims, 2 Drawing Sheets

(56) References Cited

U.S. PATENT DOCUMENTS

| | | |
|---|---|---|
| 2,255,657 A | 9/1941 | Freedman |
| 2,482,116 A | 9/1949 | Lanahan |
| 2,575,253 A | 11/1951 | Bicek |
| 2,594,086 A | 4/1952 | Smith |
| 2,605,582 A | 8/1952 | Allen |
| 2,666,428 A | 1/1954 | Glenner |
| 2,756,742 A | 7/1956 | Barton |
| 2,829,649 A | 4/1958 | Glenner |
| 2,886,004 A | 5/1959 | Morrison |
| 3,044,461 A | 7/1962 | Murdock |
| 3,486,505 A | 12/1969 | Morrison |
| 3,503,398 A | 3/1970 | Raible et al. |
| 3,570,498 A | 3/1971 | Weighton |
| 3,592,199 A | 7/1971 | Ostensen |
| 3,626,471 A | 12/1971 | Florin |
| 3,651,800 A | 3/1972 | Wilbanks |
| 3,788,318 A | 1/1974 | Dusseau et al. |
| 3,789,852 A | 2/1974 | Kim et al. |
| 3,841,317 A | 10/1974 | Awais |
| 3,875,595 A | 4/1975 | Froning et al. |
| 3,882,852 A * | 5/1975 | Sinnreich ............... 600/104 |
| 3,941,128 A | 3/1976 | Baldwin |
| 3,964,480 A | 6/1976 | Froning et al. |
| 4,013,078 A | 3/1977 | Feild et al. |
| 4,049,000 A | 9/1977 | Williams |
| 4,232,660 A | 11/1980 | Coles |
| 4,254,763 A | 3/1981 | McCready et al. |
| 4,258,716 A | 3/1981 | Sutherland |
| 4,344,419 A | 8/1982 | Burgin |
| 4,350,151 A | 9/1982 | Scott et al. |
| 4,421,108 A | 12/1983 | Cabrera et al. |
| 4,449,532 A | 5/1984 | Storz |
| 4,451,256 A | 5/1984 | Weikl et al. |
| 4,461,281 A | 7/1984 | Carson |
| 4,498,902 A | 2/1985 | Ash et al. |
| 4,513,754 A | 4/1985 | Lee et al. |
| 4,538,594 A | 9/1985 | Boebel et al. |
| 4,545,374 A | 10/1985 | Jacobson et al. |
| 4,562,832 A | 1/1986 | Wilder et al. |
| 4,573,448 A | 3/1986 | Kambin et al. |
| 4,573,454 A | 3/1986 | Hoffman |
| 4,586,491 A | 5/1986 | Carpenter |
| 4,601,713 A | 7/1986 | Fuqua et al. |
| 4,611,594 A | 9/1986 | Grayhack et al. |
| 4,617,929 A | 10/1986 | Gill |
| 4,638,799 A | 1/1987 | Moore et al. |
| 4,655,216 A | 4/1987 | Tischer |
| 4,674,501 A | 6/1987 | Greenberg |
| 4,678,459 A | 7/1987 | Onik et al. |
| 4,696,544 A | 9/1987 | Costella |
| 4,700,694 A | 10/1987 | Shishido |
| 4,716,901 A | 1/1988 | Jackson et al. |
| 4,736,738 A | 4/1988 | Lipovsek et al. |
| 4,750,475 A | 6/1988 | Yoshihashi |
| 4,750,487 A | 6/1988 | Zanetti et al. |
| 4,762,120 A | 8/1988 | Hussein |
| 4,790,297 A | 12/1988 | Luque et al. |
| 4,817,587 A | 4/1989 | Janese |
| 4,819,620 A | 4/1989 | Okutsu |
| 4,834,757 A | 5/1989 | Brantigan et al. |
| 4,837,995 A | 6/1989 | Omizono et al. |
| 4,850,342 A | 7/1989 | Hashiguchi et al. |
| 4,862,891 A | 9/1989 | Smith |
| 4,863,133 A | 9/1989 | Bonnell et al. |
| 4,875,897 A | 10/1989 | Lee et al. |
| 4,878,915 A | 11/1989 | Brantigan et al. |
| 4,887,595 A | 12/1989 | Heinig et al. |
| 4,899,729 A | 2/1990 | Gill et al. |
| 4,904,261 A | 2/1990 | Dove et al. |
| 4,905,082 A | 2/1990 | Nishigaki et al. |
| 4,921,478 A | 5/1990 | Solano et al. |
| 4,947,896 A | 8/1990 | Bartlett |
| 4,972,827 A | 11/1990 | Kishi et al. |
| 4,984,564 A | 1/1991 | Yuen |
| 5,004,457 A | 4/1991 | Wyatt et al. |
| 5,015,247 A | 5/1991 | Michelson et al. |
| 5,020,514 A | 6/1991 | Heckele et al. |
| 5,020,519 A | 6/1991 | Hayes et al. |
| 5,025,778 A | 6/1991 | Silverstein et al. |
| 5,035,706 A * | 7/1991 | Giantureo et al. ............ 606/198 |
| 5,071,410 A | 12/1991 | Pazell |
| 5,108,420 A | 4/1992 | Marks |
| 5,112,354 A | 5/1992 | Sires et al. |
| 5,125,396 A | 6/1992 | Ray |
| 5,131,382 A | 7/1992 | Meyer et al. |
| 5,133,717 A | 7/1992 | Chopin |
| 5,139,487 A | 8/1992 | Baber |
| 5,139,499 A | 8/1992 | Small et al. |
| 5,139,511 A | 8/1992 | Gill |
| 5,163,949 A | 11/1992 | Bonutti et al. |
| 5,171,279 A | 12/1992 | Mathews et al. |
| 5,190,050 A | 3/1993 | Nitzsche |
| 5,190,561 A | 3/1993 | Graber |
| 5,192,327 A | 3/1993 | Brantigan et al. |
| 5,195,507 A | 3/1993 | Bilweis |
| 5,195,541 A | 3/1993 | Obenchain |
| 5,196,023 A | 3/1993 | Martin |
| 5,197,971 A | 3/1993 | Bonutti et al. |
| 5,201,729 A | 4/1993 | Hertzmann et al. |
| 5,224,680 A | 7/1993 | Greenstein et al. |
| 5,225,001 A | 7/1993 | Manni et al. |
| 5,232,443 A | 8/1993 | Leach |
| 5,242,444 A | 9/1993 | MacMillan |
| 5,279,564 A | 1/1994 | Taylor |
| 5,287,845 A | 2/1994 | Faul et al. |
| 5,295,994 A | 3/1994 | Bonutti |
| 5,312,417 A | 5/1994 | Wilk |
| 5,313,962 A | 5/1994 | Obenchain et al. |
| 5,318,586 A * | 6/1994 | Ereren ............... 606/192 |
| 5,330,473 A | 7/1994 | Howland |
| 5,331,975 A * | 7/1994 | Bonutti ............... 128/898 |
| 5,334,150 A | 8/1994 | Kaali et al. |
| 5,339,802 A | 8/1994 | Cook |
| 5,339,803 A | 8/1994 | Mayzels |
| 5,345,927 A | 9/1994 | Bonutti et al. |
| 5,346,504 A | 9/1994 | Ortiz et al. |
| 5,353,784 A | 10/1994 | Nady et al. |
| 5,354,302 A | 10/1994 | Ko |
| 5,357,983 A | 10/1994 | Mathews et al. |
| 5,359,995 A | 11/1994 | Sewell et al. |
| 5,360,431 A | 11/1994 | Puno et al. |
| 5,364,395 A | 11/1994 | West |
| 5,370,647 A | 12/1994 | Graber et al. |
| 5,370,659 A | 12/1994 | Sakashita et al. |
| 5,373,558 A | 12/1994 | Chaum |
| 5,376,076 A | 12/1994 | Kaali et al. |
| 5,380,291 A | 1/1995 | Kaali et al. |
| 5,380,647 A | 1/1995 | Bahar |
| 5,385,583 A | 1/1995 | Cotrel et al. |
| 5,392,766 A | 2/1995 | Masterson et al. |
| 5,395,317 A | 3/1995 | Kambin |
| 5,396,880 A | 3/1995 | Kagan et al. |
| 5,397,364 A | 3/1995 | Kozak et al. |
| 5,405,360 A * | 4/1995 | Tovey ............... 606/151 |
| 5,417,203 A | 5/1995 | Tovey et al. |
| 5,431,658 A * | 7/1995 | Moskovich ............... 606/99 |
| 5,437,637 A | 8/1995 | Lieber et al. |
| 5,437,671 A | 8/1995 | Lozier et al. |
| 5,437,672 A | 8/1995 | Alleyne et al. |
| 5,439,449 A | 8/1995 | Mapes et al. |
| 5,439,464 A | 8/1995 | Shapiro et al. |
| 5,441,041 A | 8/1995 | Sauer et al. |
| 5,441,042 A | 8/1995 | Putman et al. |
| 5,443,058 A | 8/1995 | Ough et al. |
| 5,443,467 A | 8/1995 | Biedermann et al. |
| 5,443,479 A | 8/1995 | Bressi |
| 5,443,514 A | 8/1995 | Steffee et al. |
| 5,445,142 A | 8/1995 | Hassler et al. |
| 5,454,365 A | 10/1995 | Bonutti et al. |
| 5,470,333 A | 11/1995 | Ray et al. |
| 5,472,426 A | 12/1995 | Bonati et al. |
| 5,480,440 A | 1/1996 | Kambin et al. |
| 5,484,437 A | 1/1996 | Michelson et al. |
| 5,487,744 A | 1/1996 | Howland |

| | | |
|---|---|---|
| 5,489,307 A | 2/1996 | Kuslich et al. |
| 5,490,819 A | 2/1996 | Nicholas et al. |
| 5,503,617 A | 4/1996 | Jako et al. |
| 5,512,034 A | 4/1996 | Finn et al. |
| 5,514,153 A | 5/1996 | Bonutti et al. |
| 5,520,607 A | 5/1996 | Frassica et al. |
| 5,529,571 A | 6/1996 | Daniel |
| 5,534,009 A | 7/1996 | Lander et al. |
| 5,549,595 A | 8/1996 | Freitas et al. |
| 5,549,608 A | 8/1996 | Errico et al. |
| 5,549,679 A | 8/1996 | Kuslich et al. |
| 5,551,947 A | 9/1996 | Kaali et al. |
| 5,554,157 A | 9/1996 | Errico et al. |
| 5,556,371 A | 9/1996 | Schulken et al. |
| 5,556,376 A | 9/1996 | Yoon et al. |
| 5,562,696 A | 10/1996 | Nobles |
| 5,562,736 A | 10/1996 | Ray et al. |
| 5,569,205 A | 10/1996 | Hart et al. |
| 5,569,248 A | 10/1996 | Mathews et al. |
| 5,571,072 A | 11/1996 | Kronner et al. |
| 5,571,109 A * | 11/1996 | Bertagnoli ................ 606/86 A |
| 5,573,517 A | 11/1996 | Bonutti et al. |
| 5,575,754 A | 11/1996 | Konomura |
| 5,577,993 A * | 11/1996 | Zhu et al. ................ 600/204 |
| 5,586,984 A | 12/1996 | Errico et al. |
| 5,588,949 A | 12/1996 | Taylor et al. |
| 5,599,279 A * | 2/1997 | Slotman et al. ............ 600/201 |
| 5,601,554 A | 2/1997 | Howland et al. |
| 5,601,590 A | 2/1997 | Bonutti et al. |
| 5,601,690 A | 2/1997 | Gauld et al. |
| 5,603,688 A | 2/1997 | Upsher |
| 5,613,937 A | 3/1997 | Garrison et al. |
| 5,613,968 A | 3/1997 | Lin |
| 5,620,458 A | 4/1997 | Green et al. |
| 5,624,442 A | 4/1997 | Mellinger et al. |
| 5,643,282 A | 7/1997 | Kieturakis et al. |
| 5,649,902 A | 7/1997 | Yoon |
| 5,649,912 A | 7/1997 | Peterson |
| 5,662,676 A * | 9/1997 | Koninckx ................ 606/198 |
| 5,667,472 A | 9/1997 | Finn et al. |
| 5,667,473 A | 9/1997 | Finn et al. |
| 5,667,478 A | 9/1997 | McFarlin et al. |
| 5,667,520 A | 9/1997 | Bonutti et al. |
| 5,672,187 A | 9/1997 | Rock et al. |
| 5,674,295 A | 10/1997 | Ray et al. |
| 5,681,319 A | 10/1997 | Biedermann et al. |
| 5,690,606 A | 11/1997 | Slotman |
| 5,695,448 A | 12/1997 | Kimura et al. |
| 5,697,889 A * | 12/1997 | Slotman et al. ............ 600/204 |
| 5,702,454 A | 12/1997 | Baumgartner et al. |
| 5,707,359 A | 1/1998 | Bufalini et al. |
| 5,716,356 A | 2/1998 | Biedermann |
| 5,720,751 A | 2/1998 | Jackson |
| 5,725,588 A | 3/1998 | Errico et al. |
| 5,728,046 A | 3/1998 | Mayer et al. |
| 5,730,754 A | 3/1998 | Obenchain et al. |
| 5,735,792 A | 3/1998 | Vanden Hoek et al. |
| 5,755,724 A * | 5/1998 | Yoon ................ 606/114 |
| 5,755,732 A * | 5/1998 | Green et al. ............ 606/170 |
| 5,762,629 A | 6/1998 | Kambin et al. |
| 5,772,661 A | 6/1998 | Michelson et al. |
| 5,782,831 A | 7/1998 | Sherman et al. |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach et al. |
| 5,797,911 A | 8/1998 | Sherman et al. |
| 5,800,438 A * | 9/1998 | Tuke et al. ................ 606/90 |
| 5,810,809 A | 9/1998 | Rydell et al. |
| 5,810,818 A | 9/1998 | Errico et al. |
| 5,813,978 A | 9/1998 | Jako et al. |
| 5,814,084 A | 9/1998 | Grivas et al. |
| 5,817,062 A | 10/1998 | Flom et al. |
| 5,823,947 A | 10/1998 | Yoon et al. |
| 5,824,093 A | 10/1998 | Ray et al. |
| 5,827,319 A | 10/1998 | Carlson et al. |
| 5,836,948 A * | 11/1998 | Zucherman et al. .......... 606/249 |
| 5,851,214 A | 12/1998 | Larsen et al. |
| 5,857,999 A | 1/1999 | Quick et al. |
| 5,863,293 A | 1/1999 | Richelsoph |
| 5,865,728 A | 2/1999 | Moll et al. |
| 5,865,802 A | 2/1999 | Yoon et al. |
| 5,868,745 A | 2/1999 | Alleyne et al. |
| 5,873,878 A | 2/1999 | Harms et al. |
| 5,876,402 A | 3/1999 | Errico et al. |
| 5,879,389 A | 3/1999 | Koshino et al. |
| 5,882,350 A | 3/1999 | Ralph et al. |
| 5,885,286 A | 3/1999 | Sherman et al. |
| 5,888,190 A | 3/1999 | Meyer et al. |
| 5,902,231 A | 5/1999 | Foley et al. |
| 5,910,141 A | 6/1999 | Morrison et al. |
| 5,910,142 A | 6/1999 | Tatar |
| 5,921,917 A | 7/1999 | Barthel et al. |
| 5,928,137 A | 7/1999 | Green et al. |
| 5,928,232 A | 7/1999 | Howland et al. |
| 5,928,233 A | 7/1999 | Apfelbaum et al. |
| 5,954,635 A | 9/1999 | Foley et al. |
| 5,954,725 A | 9/1999 | Sherman et al. |
| 5,961,499 A | 10/1999 | Bonutti et al. |
| 5,961,517 A | 10/1999 | Biedermann et al. |
| 5,964,760 A | 10/1999 | Richelsoph et al. |
| 5,976,146 A | 11/1999 | Ogawa et al. |
| 5,976,161 A | 11/1999 | Kirsch et al. |
| 5,984,928 A | 11/1999 | Hermann |
| 5,997,471 A | 12/1999 | Gumb et al. |
| 5,997,491 A | 12/1999 | Harris |
| 5,997,508 A | 12/1999 | Lunn et al. |
| 6,004,320 A | 12/1999 | Casscells et al. |
| 6,007,487 A | 12/1999 | Foley et al. |
| 6,007,533 A | 12/1999 | Casscells et al. |
| 6,010,503 A | 1/2000 | Richelsoph et al. |
| 6,022,376 A | 2/2000 | Assell et al. |
| 6,033,406 A | 3/2000 | Mathews et al. |
| 6,036,638 A | 3/2000 | Nwawka |
| 6,042,563 A * | 3/2000 | Morejohn et al. ......... 604/96.01 |
| 6,050,997 A | 4/2000 | Mullane et al. |
| 6,051,001 A | 4/2000 | Borghi et al. |
| 6,053,917 A | 4/2000 | Sherman et al. |
| 6,063,090 A | 5/2000 | Schlapfer |
| 6,074,380 A | 6/2000 | Byrne et al. |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,111 A | 7/2000 | Nichols |
| 6,096,038 A | 8/2000 | Michelson et al. |
| 6,096,081 A | 8/2000 | Grivas et al. |
| 6,110,173 A | 8/2000 | Thomas |
| 6,110,210 A | 8/2000 | Norton et al. |
| 6,113,601 A | 9/2000 | Tatar |
| 6,120,434 A | 9/2000 | Kimura et al. |
| 6,120,437 A | 9/2000 | Yoon et al. |
| 6,126,671 A | 10/2000 | Richards et al. |
| 6,127,597 A | 10/2000 | Beyar et al. |
| 6,132,432 A | 10/2000 | Richelsoph et al. |
| 6,132,465 A | 10/2000 | Ray et al. |
| 6,139,493 A | 10/2000 | Koros et al. |
| 6,139,550 A | 10/2000 | Michelson et al. |
| 6,142,931 A | 11/2000 | Kaji et al. |
| 6,146,401 A * | 11/2000 | Yoon et al. ................ 606/192 |
| 6,162,236 A | 12/2000 | Osada et al. |
| 6,171,299 B1 | 1/2001 | Bonutti |
| 6,174,311 B1 | 1/2001 | Branch et al. |
| 6,175,758 B1 | 1/2001 | Kambin |
| 6,187,000 B1 | 2/2001 | Davison et al. |
| 6,193,715 B1 | 2/2001 | Wrublewski et al. |
| 6,206,922 B1 | 3/2001 | Zdeblick et al. |
| 6,251,111 B1 | 6/2001 | Barker et al. |
| 6,254,628 B1 | 7/2001 | Wallace et al. |
| 6,267,763 B1 | 7/2001 | Castro |
| 6,293,949 B1 | 9/2001 | Justis et al. |
| 6,306,170 B2 | 10/2001 | Ray |
| 6,312,443 B1 | 11/2001 | Stone |
| 6,338,730 B1 | 1/2002 | Bonutti et al. |
| 6,358,226 B1 | 3/2002 | Ryan |
| 6,358,266 B1 | 3/2002 | Bonutti |
| 6,361,488 B1 | 3/2002 | Davison et al. |
| 6,371,968 B1 | 4/2002 | Kogasaka et al. |
| 6,383,195 B1 | 5/2002 | Richard |

| | | |
|---|---|---|
| 6,425,859 B1 | 7/2002 | Foley et al. |
| 6,432,048 B1 | 8/2002 | Francois |
| 6,494,893 B2 | 12/2002 | Dubrul et al. |
| 6,497,654 B1 | 12/2002 | Leonard et al. |
| 6,500,206 B1 | 12/2002 | Bryan |
| 6,520,926 B2 | 2/2003 | Hall |
| 6,524,320 B2 | 2/2003 | DiPoto |
| 6,530,880 B2 | 3/2003 | Pagliuca |
| 6,530,926 B1 | 3/2003 | Davison |
| 6,562,082 B1 | 5/2003 | Leaver et al. |
| 6,564,078 B1 | 5/2003 | Marino et al. |
| 6,579,318 B2 | 6/2003 | Varga et al. |
| 6,589,225 B2 | 7/2003 | Orth et al. |
| 6,620,129 B2 | 9/2003 | Stecker et al. |
| 6,648,888 B1 | 11/2003 | Shluzas |
| 6,652,553 B2 | 11/2003 | Davison et al. |
| 6,666,866 B2 | 12/2003 | Martz et al. |
| 6,699,288 B2 | 3/2004 | Moret |
| 6,702,821 B2 | 3/2004 | Bonutti |
| 6,719,794 B2 | 4/2004 | Gerber et al. |
| 6,789,852 B1 | 9/2004 | Huang |
| 6,800,084 B2 | 10/2004 | Davison et al. |
| 6,811,558 B2 | 11/2004 | Davison et al. |
| 6,821,243 B2 | 11/2004 | Pagliuca et al. |
| 6,837,889 B2 | 1/2005 | Shluzas |
| 6,837,891 B2 | 1/2005 | Davison et al. |
| 6,887,248 B2 | 5/2005 | McKinley et al. |
| 6,916,330 B2 | 7/2005 | Simonson |
| 6,929,647 B2 | 8/2005 | Cohen |
| 7,001,397 B2 | 2/2006 | Davison et al. |
| 7,004,947 B2 | 2/2006 | Shluzas et al. |
| 7,008,424 B2 | 3/2006 | Teitelbaum |
| 7,008,431 B2 | 3/2006 | Simonson |
| 7,033,369 B2 | 4/2006 | Davison et al. |
| 7,056,321 B2 | 6/2006 | Pagliuca et al. |
| 7,066,937 B2 | 6/2006 | Shluzas |
| 7,074,226 B2 | 7/2006 | Roehm, III et al. |
| 7,079,883 B2 | 7/2006 | Marino et al. |
| 7,108,705 B2 | 9/2006 | Davison et al. |
| 7,144,393 B2 | 12/2006 | DiPoto et al. |
| 7,187,000 B2 | 3/2007 | Yang et al. |
| 7,223,278 B2 | 5/2007 | Davison et al. |
| 7,674,273 B2 * | 3/2010 | Davison et al. ............... 606/198 |
| 7,699,877 B2 | 4/2010 | Davison |
| 7,799,036 B2 | 9/2010 | Davison et al. |
| 7,850,695 B2 | 12/2010 | Pagliuca et al. |
| 7,892,171 B2 * | 2/2011 | Davison et al. ............... 600/184 |
| 7,985,237 B2 * | 7/2011 | Davison et al. ............... 606/198 |
| 8,277,486 B2 * | 10/2012 | Davison ........................ 606/249 |
| 8,317,817 B2 * | 11/2012 | Davison et al. ............... 606/198 |
| 2001/0011170 A1 | 8/2001 | Davison et al. |
| 2001/0049498 A1 | 12/2001 | Davison et al. |
| 2002/0002360 A1 | 1/2002 | Orth et al. |
| 2002/0022764 A1 | 2/2002 | Smith et al. |
| 2002/0055745 A1 | 5/2002 | McKinley et al. |
| 2002/0143235 A1 | 10/2002 | Pagliuca |
| 2002/0165612 A1 | 11/2002 | Gerber et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0083688 A1 | 5/2003 | Simonson |
| 2003/0083689 A1 | 5/2003 | Simonson |
| 2003/0083998 A1 | 5/2003 | Ramachandran et al. |
| 2003/0108203 A1 | 6/2003 | Sambhwani et al. |
| 2003/0139648 A1 | 7/2003 | Foley et al. |
| 2003/0153911 A1 | 8/2003 | Shluzas |
| 2003/0153927 A1 | 8/2003 | DiPoto et al. |
| 2003/0153928 A1 | 8/2003 | El-Galley |
| 2003/0167058 A1 | 9/2003 | Shluzas |
| 2003/0191371 A1 | 10/2003 | Smith et al. |
| 2003/0191381 A1 | 10/2003 | Luce |
| 2003/0195405 A1 | 10/2003 | Marino et al. |
| 2003/0195493 A1 | 10/2003 | Davison et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199871 A1 | 10/2003 | Foley et al. |
| 2003/0199885 A1 | 10/2003 | Davison et al. |
| 2003/0236529 A1 | 12/2003 | Shluzas et al. |
| 2004/0059339 A1 | 3/2004 | Roehm et al. |
| 2004/0078051 A1 | 4/2004 | Davison et al. |
| 2004/0082960 A1 | 4/2004 | Davison |
| 2004/0090812 A1 | 5/2004 | Takashima |
| 2004/0093002 A1 | 5/2004 | Davison et al. |
| 2004/0097907 A1 | 5/2004 | DiPoto |
| 2004/0098012 A1 | 5/2004 | Davison et al. |
| 2004/0116954 A1 | 6/2004 | Pagliuca et al. |
| 2004/0133201 A1 | 7/2004 | Shluzas et al. |
| 2004/0176665 A1 | 9/2004 | Branch et al. |
| 2004/0176763 A1 | 9/2004 | Foley et al. |
| 2004/0236317 A1 | 11/2004 | Davison |
| 2005/0021030 A1 | 1/2005 | Pagliuca et al. |
| 2005/0033297 A1 | 2/2005 | Davison |
| 2005/0043754 A1 | 2/2005 | Davison et al. |
| 2005/0075540 A1 | 4/2005 | Shluzas et al. |
| 2005/0113833 A1 | 5/2005 | Davison |
| 2006/0089662 A1 | 4/2006 | Davison et al. |
| 2006/0264999 A1 | 11/2006 | Davison et al. |
| 2006/0276821 A1 | 12/2006 | Davison et al. |
| 2006/0276822 A1 | 12/2006 | Davison et al. |
| 2006/0293678 A1 | 12/2006 | Davison et al. |

FOREIGN PATENT DOCUMENTS

| | | |
|---|---|---|
| DE | 2222979 A1 | 11/1973 |
| DE | 3108766 C2 | 12/1983 |
| DE | 3936811 A1 | 9/1990 |
| EP | 0303824 A3 | 2/1989 |
| EP | 0528562 A | 2/1993 |
| EP | 0528562 A3 | 2/1993 |
| EP | 0305077 B1 | 5/1994 |
| EP | 0980677 A1 | 2/2000 |
| EP | 0682918 B1 | 5/2000 |
| EP | 1251878 A3 | 10/2002 |
| EP | 0807415 B1 | 12/2003 |
| EP | 1090595 B1 | 12/2003 |
| EP | 1251767 A4 | 9/2009 |
| EP | 1305077 A4 | 10/2009 |
| FR | 2701379 B1 | 4/1995 |
| FR | 2714285 B1 | 3/1996 |
| GB | 2234906 A | 2/1991 |
| JP | 2000083960 A | 3/2000 |
| JP | 2001149376 A | 6/2001 |
| TW | 0137324 | 7/1990 |
| TW | 0141205 | 9/1990 |
| WO | 8303189 A1 | 9/1983 |
| WO | 9106266 A1 | 5/1991 |
| WO | 9219146 A1 | 11/1992 |
| WO | 9221292 A3 | 2/1993 |
| WO | 9314801 A1 | 8/1993 |
| WO | 9315647 A1 | 8/1993 |
| WO | 9403114 A1 | 2/1994 |
| WO | 9510218 A1 | 4/1995 |
| WO | 9522285 A1 | 8/1995 |
| WO | 9532663 A1 | 12/1995 |
| WO | 9833462 A1 | 8/1998 |
| WO | 9837884 A1 | 9/1998 |
| WO | 0018306 A1 | 4/2000 |
| WO | 0154560 A3 | 2/2002 |
| WO | 0209801 A1 | 2/2002 |
| WO | 02022030 A3 | 9/2002 |
| WO | 0278767 A3 | 2/2003 |
| WO | 02078767 A3 | 2/2003 |
| WO | 03007783 A3 | 9/2003 |
| WO | 2004021899 A1 | 3/2004 |
| WO | 2004039235 A3 | 8/2004 |

OTHER PUBLICATIONS

Endius, Atavi Atraumatic Spine Fusion System Marketing Bulletin, "Minimally Invasive Update on Danek," Apr. 12, 2002.

Endius, Atavi Atraumatic Spine Fusion System Marketing Bulletin, "How Do I Decompress Using Atavi System?", Mar. 4, 2002.

"Arthroscopic Microdiskectomy" by Kambin, Mount Sinai J. of Medicine, pp. 159-164 (Mar. 1991).

Liu et al., "Posterior Fusion of the Subaxial Cervical Spine: Indications and Techniques," Neurosurgery Focus 4 (10): Article 7, Apr. 2001.

Kambin, "Diagnostic and Therapuetic Spinal Arthroscopy," Neurosurgery Clinics of North America, 1 (7): 65-76, 1996.
Caspar, Wolfhard, M.D. et al. "The Caspar Microsurgical Discectomy and Comparison with a Conventional Standard Lumbar Disc Procedure," Neurosugery, Jan. 1991, pp. 78-87, vol. 28, No. 1, Williams & Wilkins, Baltimore, MD.
Musculoskeletal Transplant Foundation presentation material (2 pgs.) entitled The MTF EndoDower, dated Jun. 1996.
Musculoskeletal Transplant Foundation presentation material (1-16) Apr. 1996.
Albee, An Excerpt from Bone Graft Surgery in Disease, Injury and Deformity, Preface: xi-x, 1940.
Vich, "Anterior Cervical Interbody Fusion with Threaded Cylindrical Bone," J. Neurosurg, vol. 63: 750-753, 1985.
U.S. Appl. No. 07/328,952, Material cancelled from Meyer Application. Mailed Mar. 27, 1989, publicly available at least on Jul. 21, 1992.
Stauber et al., "Pedicle Screw Placement with Intrasseous Endoscopy," SPINE, 1 (19): 57-61, 1994.
Destandau, "A Special Device for Endoscopic Surgery of Lumbar Disc Herniation," Neurological Research, vol. 21: 39-42, Jan. 1999.
Ditsworth, "A New and Superior Technique for Removal of Herniated Lumbar Disc: Endoscope and Nucleotome Combination," The Joint Section on Spine and Peripheral Nerves, Abstract, Feb. 1995.
Ditsworth, "Endoscopic Transforaminal Lumbar Discectomy and Reconfiguration: A Posterolateral Approach Into the Spinal Canal," Surg. Neurol., 49: 588-598, 1998.
EndiusTM presentation materials, "Spine Endoscopy System with FlexPosure," 2 pgs., 1999.
Foley et al., "Percutaneous Pedicle Screw Fixation of the Lumbar Spine," Neurosurg. Focus, 4 (10): Apr. 1-8, 2001.
Guiot et al., "A Minimally Invasive Technique for Decompression of the Lumbar Spine," 4 (27): 432-438, 2002.
Kambin, "Arthroscopic Microdiscectomy," The Adult Spine: Principles and Practice, 94: 2023-2036, 1997.
Kambin, "Arthroscopic Lumbar Interbody Fusion," Spine Care White AH, 77: 1055-1056, 1995.
Kambin, "Arthroscopic Lumbar Intervertebral Fusion," The Adult Spine, Principals and Practice, 95: 2037-2046, 1997.
Kambin, "Arthroscopic Techniques for Spinal Surgery," Operative Arthroscopy, Second Edition, 89: 1215-1225, 1996.
Kambin, "Endoscopic Laminotomy Procedures," On sale and in public use in the United States more than one year prior to Aug. 1, 2000.
Kambin, "Posterolateral Percutaneous Lumbar Interbody Fusion," Arthroscopic Microdiscectomy, Minimal Intervention in Spinal Surgery, 9: 117-121, 1991.
Kambin, "The Role of Minimally Invasive Surgery in Spinal Disorders," Advances in Operative Orthopaedics, vol. 3: 147-171, 1995.
Sofamor Danek presentation materials, "Laparoscopic Bone Dowel Surgical Technique," 17 pgs., 1995.
Leonard Medical Inc., Brochure Entitled, "Instruments for Less Invasive Surgery," 6 pgs., prior to Aug. 1, 2000.
Mathews, "Spinal Endoscopy Evolution, Applications & Foundations," 1-44, on or before Oct. 25, 2002.
MED presentation materials, "MicroEndoscopic Discectomy System," 33 pgs., 1997.
Medtronic Sofamor Danek, "An Evolution in Minimally Invasive Spine Surgery," METRx, MicroEndoscopic Discectomy, 6 pgs., 1999.
Medtronic Sofamor Danek, "METRx Microdiscectomy Surgical Technique," as described by Donald L. Hilton Jr., M.D., F.A.C.S. and Sylvain Palmer, F.A.C.S., 19 pgs., 2001.
Medtronic Sofamor Danek, "The Next Step in Minimally Invasive Discectomy Utilizing the Operating Microscope," 2 pgs., 2000.
Sofamor Danek brochure, "Micro-Endo Systems," 2 pgs., 1994.
Sofamor Danek brochure, "Laparoscopic Bone Dowel Instruments," 2 pgs., 1995.
Request for Declaration of Interference filed in U.S. Appl. No. 10/734,161, filed Jan. 29, 2004.
Caspar, Wolfhard, M.D.; "The Caspar Microsurgical Discectomy and Comparison with a Conventional Standard Lumbar Disc Procedure" Neurosurgery, vol. 28, No. 1; pp. 78-87, Jan. 1991.
Ditsworth, David A., M.D.; "Endoscopic Transforaminal Lumbar Discectomy and Reconfiguration: A Posterolateral Approach into the Spinal Canal", Surgery & Neurology, Chapter 49; pp. 588-598.; 1998.
Endius Marketing Bulletin for the Atavi Atraumatic Spine Fusion System entitled, "How do I decompress using Atavi System?"; 2002.
Endius Marketing Bulletin for the Atavi Atraumatic Spine Fusion System entitled, "Minimally Invasive Update on Danek"; 2002.
Foley, Kevin T., M.D. et al.; "Percutaneous Pedicle Screw Fixation of the Lumbar Spine"; Neurosurgery Focus, No. 10; pp. 1-8; Apr. 2001.
Guiot, Bernard H., M.S. et al.; "A Minimally Invasive Technique for Decompression of the Lumbar Spine", SPINE, vol. 27, No. 4; pp. 432-438; 2002.
Kambin, Parviz, M.D. and Jonathan L. Schaffer, M.D.; "Arthroscopic Fusion of the Lumbosacral Spine"; Lumbosacral and Spinopelvic Fixation, Chapter 44; pp. 565-577; 1996.
Kambin, Parviz, M.D.; "Arthroscopic Lumbar Interbody Fusion"; Chapter 77; pp. 1055-1066, date unknown.
Kambin, Parviz, M.D.; "Arthroscopic Lumbar Intervertebral Fusion", The Adult Spine: Principles and Practice, Chapter 95; pp. 2037-2046; 1997.
Kambin, Parviz; M.D.; "Arthroscopic Microdiskectomty"; Mount Sinai Journal of Medicine; vol. 3; pp. 159-164; 1991.
Kambin, Parviz, M.D.; "Arthroscopic Techniques for Spinal Surgery", Operative Arthroscopy, Second Edition; Chapter 89; pp. 1215-1225; 1996.
Kambin, Parviz, "Diagnostic and Therapeutic Spinal Arthroscopy," Neurosurgery Clinics of North America, 7(1):65-76, 1996.
Kambin, Parviz, M.D.; "Posterolateral Percutaneous Lumbar Interbody Fusion"; Chapter 9; pp. 117-121, date unknown.
Kambin, Parviz, "The Role of Minimally Invasive Spine Surgery," Advances in Operative Orthopaedics, 3:147-171, 1995.
Medtronic Sofamor Danek, "METRx Microdiscectomy Surgical Technique, 2001 as described by Donald L. Hilton, Jr., M.D., F.A.C.S. and Sylvain Palmer, M.D., F.A.C.S."; date unknown.
Medtronic Sofamor Danek; "Minimal Access Spinal Technologies"; Orthopedics Today; pp. 1-20; 2002.
Medtronic Sofamor Danek promotional material for the METRx MicroEndoscopic Discectomy System entitled, "An Evolution in Minimally Invasive Spine Surgery"; 1999.
Medtronic Sofamor Danek promotional material for the METRx MicroDiscectomy System entitled, "The Next Step in Minimally Invasive Discectomy Utilizing the Operating Microscope"; 2000.
Sofamor Danek USA; A manual entitled "MED.TM. MicroEndoscopic Discectomy System by Sofamor Danek USA"; pp. 1-33; 1996.
Stauber, Martin H., M.D. et al., "Pedicle Screw Placement with Intraosseous Endoscopy", SPINE, vol. 19, No. 1; pp. 57-61; 1994.

* cited by examiner

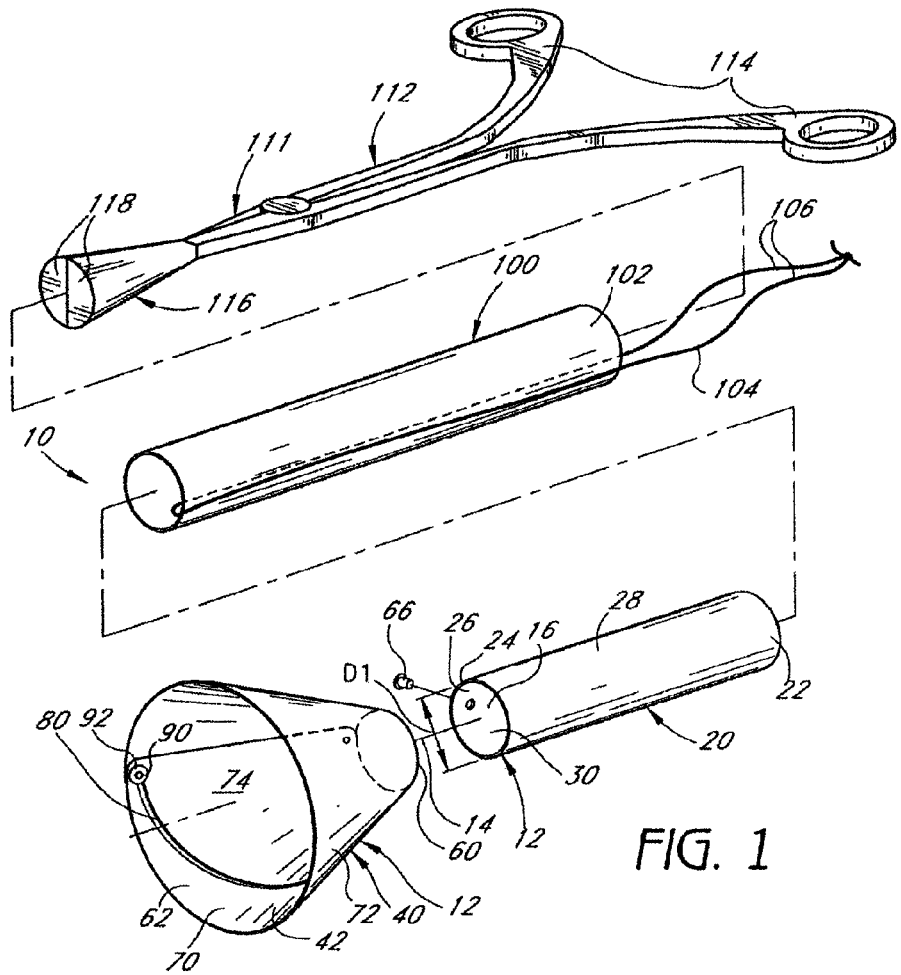
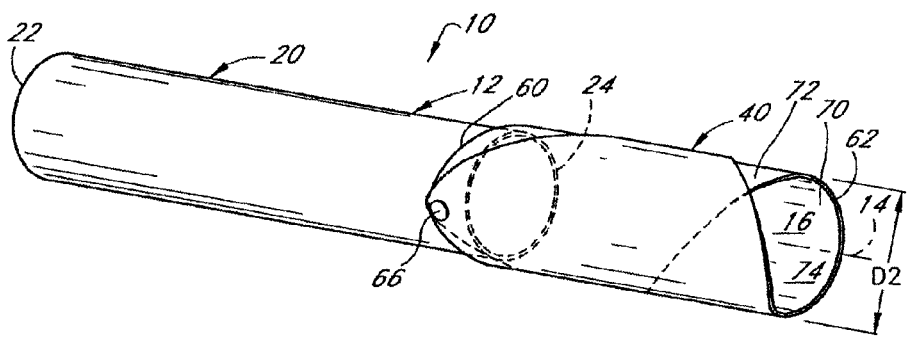

CANNULA FOR RECEIVING SURGICAL INSTRUMENTS

CROSS-REFERENCE TO RELATED APPLICATIONS

This application is a continuation of Ser. No. 11/417,616, filed May 3, 2006, which is a continuation of U.S. application Ser. No. 10/440,278, filed May 16, 2003, now U.S. Pat. No. 7,108,705, which is a continuation of U.S. application Ser. No. 09/772,605, filed Jan. 30, 2001, now U.S. Pat. No. 6,800,084, which is a continuation-in-part of U.S. application Ser. No. 09/137,335, filed Aug. 20, 1998, now U.S. Pat. No. 6,187,000, the entire disclosures of which are incorporated herein by reference.

TECHNICAL FIELD

The present invention is directed to a cannula for receiving surgical instruments for performing a surgical procedure on a body.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a cannula for receiving surgical instruments for performing a surgical procedure on a body. The cannula comprises a tube structure defining a passage through which the surgical instruments are inserted into the body. The tube structure has a proximal end and a distal end. The tube structure includes an expandable portion for enabling an increase in the cross-sectional area of the passage at least at the distal end.

The expandable portion of the tube structure, when expanded, has a conical configuration. The expandable portion of the tube structure includes an arcuate slot and a guide pin disposed in the arcuate slot. The guide pin is movable from a terminal end of the slot to a second terminal end of the slot to enable the cross-sectional area of the passage at the distal end to increase.

The tube structure includes first and second tubular portions attached to one another. The second tubular portion comprises the expandable portion. The first tubular portion comprises a length of stainless steel tubing and the second tubular portion comprises an arcuate segment of stainless steel sheet stock rolled into a tubular shape.

BRIEF DESCRIPTION OF THE DRAWINGS

The foregoing and other features of the present invention will becomes apparent to one skilled in the art to which the present invention relates upon consideration of the following description of the invention with reference to the accompanying drawings, wherein:

FIG. 1 is an exploded perspective view of a surgical cannula constructed in accordance with the present invention, the cannula being shown in an expanded condition;

FIG. 2 is a perspective view of the cannula of FIG. 1 with parts removed for clarity, the cannula being shown in a contracted condition;

DETAILED DESCRIPTION OF THE PREFERRED EMBODIMENT

Figure 4:
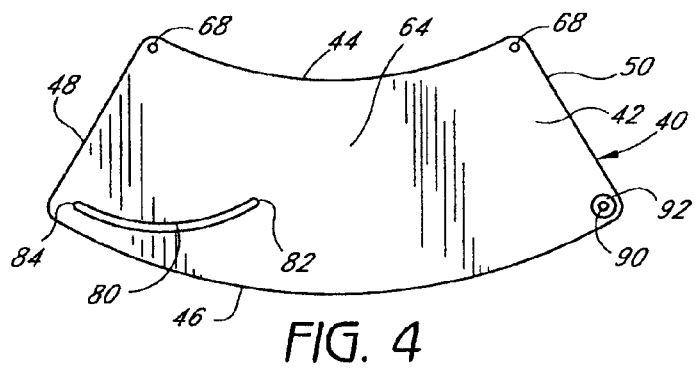
FIG. 4 is a roll out view of a part of the cannula of FIG. 1.

The present invention is directed to a cannula for receiving surgical instruments for performing a surgical procedure on the body of a patient. The present invention is applicable to a variety of surgical procedures in which endoscopic surgical techniques are used.

FIG. 1 illustrates a cannula 10 constructed according to the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 20 mm.

The second tubular portion 40 of the tubular structure 12 is attached to the distal end 24 of the first tubular portion 20. The second tubular portion is preferably made from stainless steel, but could alternatively be made from another suitable material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured an inner end of the guide pin 90 to retain the guide pin in the arcuate slot 80.

Figure 3:
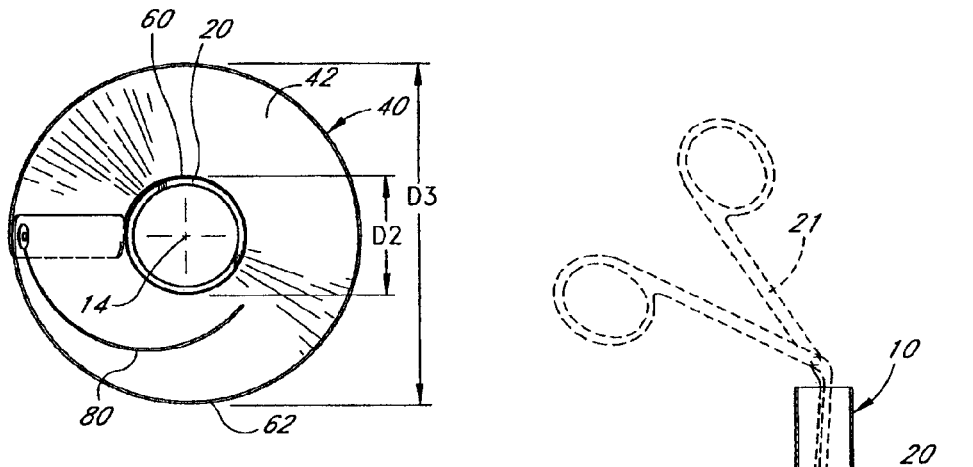
FIG. 3 is a schematic end view showing the cannula of FIG. 1 in the expanded position.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60. Thus, in the expanded condition, the cross-sectional area of the second passage portion 74 at the second end 62 of the second tubular portion 40, which is function of the diameter D3, is 40% to 80% greater than the cross-sectional area of the second passage portion at the first end 60 of the second tubular portion.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of nylon string 104 for tearing the heat shrunk tubing 102 is wrapped around the heat shrunk tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a preferred embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted into the body of a patient in the contracted condition. The outer end 106 of the string 104 is then manually pulled on by the surgeon. Pulling on the string 104 tears the heat shrunk tubing 102 which is then removed from the cannula 10 by the surgeon. With the heat shrink tubing 102 removed, the second tubular portion 40 of the cannula 10 is thereby released for expansion toward the expanded condition.

Figure 5:
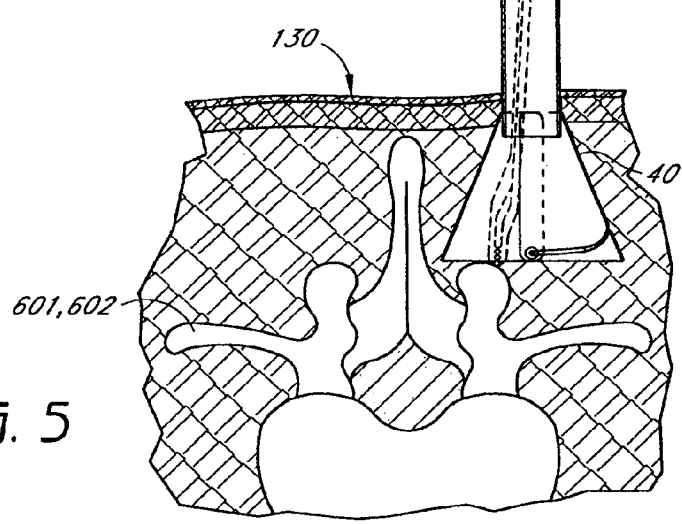
FIG. 5 is a schematic sectional view of the cannula of FIG. 1 during a surgical procedure.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 10.

It is contemplated that the cannula 10 described herein could be the centerpiece of a endoscopic surgical kit which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

What is claimed:

1. A method of accessing a spinal surgical site in a patient, the method comprising:
providing an access device having an elongate body with a proximal end and a distal end and defining a length between the proximal and distal ends, the access device having an outer surface for engaging the body of a patient and an inner surface at least partially defining a passage sized for receiving a plurality of surgical instruments used to perform a surgical procedure, the access device including an actuatable portion that is actuatable between an unexpanded configuration for insertion into the patient and an expanded configuration for retracting tissue to provide an enlarged surgical field at the spinal surgical site, wherein a cross-sectional area of the passage at a first location in the expanded configuration is greater than a cross-sectional area of the passage at a second location, wherein the first location is distal of the second location;

providing an actuator configured to move the actuatable portion from the unexpanded configuration to the expanded configuration;

inserting the access device into the patient such that the distal end is adjacent the spinal surgical site and the proximal end is outside the patient;

moving the access device from the unexpanded configuration to the expanded configuration with the actuator, thereby increasing access to the spinal surgical site;

delivering more than one surgical instrument along an entire length of the passage to the spinal surgical site; and removing the actuator from the access device, wherein the access device remains in the expanded configuration.

2. The method of claim 1, wherein the actuator is configured to be inserted into the passage, wherein the step of moving the access device from the unexpanded configuration to the expanded configuration includes engaging the inner surface of the access device with the actuator and applying a radially directed force against the inner surface.

3. The method of claim 2, wherein after the step of moving the access device, the method further comprises removing the actuator from the access device, wherein the access device remains in the expanded configuration.

4. The method of claim 1, further comprising performing a surgical procedure through the access device at the spinal surgical site.

5. The method of claim 1, wherein the access device comprises a first member and a second member moveable relative to each other.

6. A method of accessing a spinal surgical site in a patient, the method comprising:

providing an access device having an elongate body with a proximal end and a distal end and defining a length between the proximal and distal ends, the access device having an outer surface for engaging the body of a patient and an inner surface at least partially defining a passage sized for receiving a plurality of surgical instruments used to perform a surgical procedure, the access device including an actuatable portion that is actuatable between an unexpanded configuration for insertion into the patient and an expanded configuration for retracting tissue to provide an enlarged surgical field at the spinal surgical site, wherein a cross-sectional area of the passage at a first location in the expanded configuration is greater than a cross-sectional area of the passage at a second location, wherein the first location is distal of the second location;

providing an actuator configured to move the actuatable portion from the unexpanded configuration to the expanded configuration;

inserting the access device into the patient such that the distal end is adjacent the spinal surgical site and the proximal end is outside the patient;

moving the access device from the unexpanded configuration to the expanded configuration with the actuator, thereby increasing access to the spinal surgical site; and delivering more than one surgical instrument along an entire length of the passage to the spinal surgical site;

wherein the actuator is configured to be inserted into the passage, wherein the step of moving the access device from unexpanded configuration to the expanded configuration includes engaging the inner surface of the access device with the actuator and applying a radially directed force against the inner surface.

7. The method of claim 6, further comprising the step of removing the actuator from the access device, wherein the access device remains in the expanded configuration.

8. The method of claim 6, wherein after the step of moving the access device, the method further comprises removing the actuator from the access device, wherein the access device remains in the expanded configuration.

9. The method of claim 6, further comprising performing a surgical procedure through the access device at the spinal surgical site.

10. The method of claim 6, wherein the access device comprises a first member and a second member moveable relative to each other.

* * * * *